(12) United States Patent
Nozoe et al.

(10) Patent No.: US 6,777,677 B2
(45) Date of Patent: Aug. 17, 2004

(54) METHOD OF INSPECTING PATTERN AND INSPECTING INSTRUMENT

(75) Inventors: Mari Nozoe, Hino (JP); Hidetoshi Nishiyama, Kokubunji (JP); Shigeaki Hijikata, Ome (JP); Kenji Watanabe, Ome (JP); Koji Abe, Hitachinaka (JP)

(73) Assignees: Hitachi, Ltd., Tokyo (JP); Hitachi Tokyo Electronics Co., Ltd., Tokyo (JP)

( * ) Notice: Subject to any disclaimer, the term of this patent is extended or adjusted under 35 U.S.C. 154(b) by 0 days.

(21) Appl. No.: 10/463,576

(22) Filed: Jun. 18, 2003

(65) Prior Publication Data

US 2003/0213909 A1 Nov. 20, 2003

Related U.S. Application Data

(63) Continuation of application No. 09/725,900, filed on Nov. 30, 2000, now Pat. No. 6,583,414.

(30) Foreign Application Priority Data

Dec. 2, 1999 (JP) .......................................... 11-343094

(51) Int. Cl.⁷ ........................ H01J 37/28; G01N 23/225
(52) U.S. Cl. ........................ 250/310; 250/307; 282/141
(58) Field of Search ................................ 250/306, 307, 250/310, 442.1, 491.1; 382/144, 145, 155.1

(56) References Cited

U.S. PATENT DOCUMENTS

| | | |
|---|---|---|
| 4,870,344 A | 9/1989 | Stille |
| 5,085,517 A | 2/1992 | Chadwick et al. |
| 5,182,454 A * | 1/1993 | Matsuda et al. ............ 250/310 |
| 5,502,306 A | 3/1996 | Meisburger et al. |
| 5,717,204 A | 2/1998 | Meisburger et al. |
| 5,777,327 A | 7/1998 | Mizuno |
| 5,909,276 A | 6/1999 | Kinney et al. |
| 6,038,018 A | 3/2000 | Yanazaki et al. |
| 6,047,083 A * | 4/2000 | Mizuno ...................... 382/141 |
| 6,172,363 B1 | 1/2001 | Shinada et al. |
| 6,329,826 B1 | 12/2001 | Shinada et al. |
| 6,348,690 B1 | 2/2002 | Iwabuchi et al. |
| 6,353,222 B1 * | 3/2002 | Dotan ........................ 250/310 |
| 6,426,501 B1 * | 7/2002 | Nakagawa .................. 250/310 |

FOREIGN PATENT DOCUMENTS

| | | |
|---|---|---|
| JP | 3-167456 | 7/1991 |
| JP | 5-258703 | 10/1993 |
| JP | 9-138198 | 5/1997 |
| JP | 9-184715 | 7/1997 |
| JP | 10-135288 | 5/1998 |
| JP | 10-234543 | 9/1998 |

OTHER PUBLICATIONS

Journal of Vacuum Science & Technology B, vol. 9, No. 6, pp. 3005–3009 (1991).
Journal of Vacuum Science & Technology B, vol. 10, No. 6, pp. 2804–2808 (1992).

* cited by examiner

*Primary Examiner*—John R. Lee
*Assistant Examiner*—James J. Leybourne
(74) *Attorney, Agent, or Firm*—Antonelli, Terry, Stout & Kraus, LLP

(57) ABSTRACT

A pattern inspection system for inspecting a substrate surface on which a predetermined pattern is formed with radiation of an electron beam and an optical beam. the pattern inspection system includes a radiation and which radiates an electron beam to the substrate, a detection unit which detects a secondarily generated signal attributable to the radiation of the electron beam, a retrieval unit which retrieves an image from the signal detected by the detection unit, and an image processing unit which classifies the retrieved image depending on a type of the image.

7 Claims, 7 Drawing Sheets

FIG.5

| REVIEW MODE \ PARAMETER | FIGURE REVIEW MODE | VOLTAGE CONTRAST REVIEW MODE | ROUGHNESS REVIEW MODE |
|---|---|---|---|
| BEAM CURRENT | 3pA~50pA | 50pA~200pA | INPUT NOT REQUIRED |
| DETECTOR | SECONDARY ELECTRON DETECTOR (THE SECOND DETECTOR) | DETECTOR FOR SECONDARY ELECTRON WHICH (THE THIRD DETECTOR) | REFLECTED ELECTRON DETECTOR (THE FIRST DETECTOR) |
| SCAN SPEED | TV SCAN | TV SCAN(OPEN DEFECT) SLOW SCAN(SHORT DEFECT) | INPUT NOT REQUIRED |
| BEAM IRRADIATION ENERGY | 800V~1kV | 500V~800V | INPUT NOT REQUIRED |

METHOD OF INSPECTING PATTERN AND INSPECTING INSTRUMENT

CROSS REFERENCE TO RELATED APPLICATION

This is a continuation of U.S. application Ser. No. 09/725,900, filed Nov. 30, 2000, now U.S. Pat. No. 6,583,414, the subject matter of which is incorporated by reference herein.

BACKGROUND OF THE INVENTION

The present invention relates to a method and an instrument for manufacturing elements including micro-miniature patterns on a substrate and particularly to an inspecting instrument and a method of inspecting micro-miniature patterns such as the circuits or the like in a semiconductor device and a liquid crystal device and more particularly to an inspecting instrument and a method of inspecting patterns on a wafer that is placed in the course of manufacture of semiconductor device and a method of manufacturing a semiconductor device using the same.

A related art will be explained using an example of inspection of a semiconductor wafer.

A semiconductor device can be manufactured by repeating the process to transfer the patterns formed mainly on a photo-mask to the semiconductor wafer with the lithography and etching steps. In the semiconductor device manufacturing process, since adequacy of lithography step, etching step and the other various steps and generation of particle will give large influence on the manufacturing yield of semiconductor device, the method of inspecting the patterns on the semiconductor wafer in the manufacturing process has been introduced in order to quickly or previously detect generation of irregularity and defect and then feed back such data to the manufacturing process.

As a method of inspecting the defect existing in the patterns formed on a semiconductor wafer, a defect inspecting instrument has been put into the practical use to irradiate a semiconductor wafer with the white light and compare the circuits patterns of the same type of a plurality of LSIs using an optical image. For example, in the inspecting method using an optical image, a method of detecting a defect has been disclosed as described in the JP-A No. H3-167456 in order to focus the light beam to the optical lighting area on the substrate with a time delay integration sensor and then compare such focused image with the previously input design information.

Moreover, the JP-A No. H9-138198 discloses a method of inspecting only particle or defect by detecting the diffracted light beam or scattered light beam through radiation of laser beam and then discriminating the regular diffracted light beam from the circuit pattern and the scattered light beam from particle or defect of irregular shape.

Moreover, with introduction of micro-miniaturization of circuit pattern, complicated shape of circuit pattern and versatile materials, it has now become difficult to detect the defect of optical image. Therefore, there is proposed an inspection method through comparison of circuit patterns using an electron beam image having the higher resolution that of the optical image.

As the pattern comparison inspection instrument using electron beam, Journal of Vacuum Science & Technology B, Vol. 9, No. 6., pp. 3005–3009 (1991), Journal of Vacuum Science & Technology B, Vol.10, No. 6, pp.2804–2808 (1992), JP-A No. H5-258703, U.S. Pat. No. 5,502,306 and JP-A No. H10-234543 disclose a method to automatically detect a defect by irradiating a conductive substrate (X-ray mask or the like) with the electron beam having an electron beam current that is 1000 times or more (10 nA or more) the ordinary SEM, detecting any one of generated secondary electron, reflected electron and transmitting electron and then comparing the image formed from such signal for the inspection purpose. This inspecting method is called hereinafter the wafer inspection system using electron beam.

In the wafer inspection using electron beam, an image having the resolution higher than that of the wafer inspection system or the inspection using laser can be obtained. Therefore, an ultra-miniature particle or defect on a micro-miniature circuit pattern can be detected. In addition, conductivity/non-conductivity of circuit pattern, electrical defect such as wiring and short-circuit of transistor generated at the surface or lower layer can be detected from voltage contrast reflecting potential difference at the surface on the secondary electron radiation efficiency due to the influence of charging by radiation of electron beam. The voltage contrast and the technology using the same are disclosed on the pages 839 to 841 of the "ELECTRON, ION BEAM HANDBOOK" (Published by Nikkan Kogyo Shimbun Co. Ltd.).

In the wafer inspection system and inspection using the laser, particle and defect of circuit pattern shape are detected. For the particle and defect detected, it is required to observe in detail the contents thereof in order to identify the cause of generation. Therefore, a method is now employed to receive the positional information of particle or defect detected with each inspection instrument through a communication network or medium and observe such information in the high magnification factor and high resolution with an optical microscope unit image, laser microscope unit image or electron beam image. With development in micro-miniaturization of pattern and defect or particle detected, an electron beam image can be observed in detail with the higher resolution in comparison with the optical microscope unit image or laser microscope unit image. Therefore, the observation method by the electron beam image is now widely employed. The observation instrument using such electron beam image is called, hereinafter, the review SEM.

The review SEM and an observing method in this review SEM are respectively disclosed in the JP-A No. H9-184715 and No. H10-135288. In regard to the particle and pattern defect detected with the wafer inspection system and laser inspection system as explained above, detail shape observation has become possible using the review SEM that can allocate the observation area and observe this area with the electron beam image by receiving the positional information of these inspection instruments.

However, in the wafer inspection system using electron beam, an electrical defect such as short-circuit or disconnection of transistors generated in the lower layer even if there is no irregular phenomenon in the shape of surface can be detected through the voltage contrast. It has been attempted to observe the detail of such electrical defect detected with such wafer inspection system using electron beam with an ordinary SEM, wafer inspection system or review SEM but it has been accompanied with the problem that voltage contrast cannot be obtained, disabling the observation. Regarding this problem, the review SEM that enables both high resolution observation of particle and pattern shape defect and detail observation of electrical defect that can be realized with voltage contrast has not yet been proposed in the related art.

As is explained above regarding the related art, as a result of application of wafer inspection system using laser in addition to wafer inspection system and inspection system using laser to various ultra-fine circuit patterns as well as semiconductor device, it has become possible now to detect the defects such as particle and pattern figure defect and various defects such as electrical defects like the open/short-circuit of transistors and the defects such as conductivity defect of hole pattern or the like that cannot be detected only from the figure of surface.

In order to improve the circuit pattern manufacturing process based on the result of defect detection with the wafer inspection system using electron beam, it is necessary to review in detail the contents of detected defect and execute the detail classification of particle, defect in the figure and electrical defect or the like to identify the cause of generated defect from the review result and classification result.

On the occasion of reviewing irregularity and particle in the figure of surface using the review SEM, it is effective to introduce a method of reviewing the SEM image that can be obtained by irradiating the review area under the high resolution condition that is realized with the electron beam squeezed to narrow beam and then detecting the generated secondary electron beam. In the case of SEM image, since the surface roughness information is included in the reflected electron generated when the review object is irradiated with the electron beam, it is effective to introduce a method to detect and review the reflected electron including the surface roughness information on the occasion of reviewing the surface height condition of the review object. Therefore, in order to simultaneously review the figure and material information and surface roughness information, it is preferable to install a plurality of detectors to discriminate and detect the figure and material information and the surface roughness information. On the other hand, the observation conditions such as electron beam current and scan speed or the like that are suitable for review of electrical defects from the voltage contrast are different from the conditions that are suitable for review of surface figure defect and particle.

In the cited references, the review SEM for reviewing in high resolution the surface and particle figures has been described, but these also include a problem that the observation conditions that are suitable for observation of electrical defects cannot be set easily. Thereby, this review SEM has always been accompanied with the problem that the electro-optical conditions must be manually set depending on the review purpose and therefore adjustment requires a large amount of time and labor.

Moreover, in the review SEM, it is required to receive the positional information of the defect detected with various kinds of inspection instruments with communication or medium and an image of defect is formed by scanning to the defective position and therefore high accuracy positioning is necessary to review fine particle and defect. In the method and instrument of the related art, rotation has been compensated through the alignment using the patterns of two points on the wafer 2 as the review object, but such compensation has a problem in reception of positional information pieces among various instruments that a delicate deviation is generated in the magnification factor of coordinate system and in the positional information and thereby the position is displaced at the time of extracting the sight of defective position.

Moreover, in various inspection instruments, various inspections are executed for the wafers that are manufactured from time to time in the semiconductor manufacturing process. Therefore, a large amount of particles and defects can be detected. It is of course required to know the detail contents of the detected defect and particles, but in this case, a problem rises that a large amount of time is required in such a case that all defects of all wafers are reviewed with the existing review SEM. Therefore, it has been requested to select the review areas from a large amount of defects for the highly efficient detection of characteristics of defects. Moreover, it has also been required to review and classify the selected defects automatically at a higher speed.

SUMMARY OF THE INVENTION

It is a first object of the present invention to provide a pattern inspecting instrument and a method of inspecting pattern for inspecting a fine pattern such as a circuit on the substrate surface of semiconductor device or the like by radiating thereto a white beam, laser beam or electron beam in order to efficiently inspect, review and discriminate, within a short period, various particles and defects such as the detected surface roughness, defect of figures and particles and moreover electrical defects.

Moreover, it is a second object of the present invention to provide a pattern inspecting instrument and a method of inspecting pattern for realizing high-speed and highly accurate review and classification of various particles and defects explained above.

Moreover, it is a third object of the present invention to provide an inspection instrument and an inspection method that assure, through application to various kinds of semiconductor devices in multiple steps and the other fine circuit patterns in the earlier stage, highly efficient detection of process defect of semiconductor device or the like, reflection of the result on the manufacturing conditions, enhancement of reliability of semiconductor device and reduction of failure rate.

Particles and figure defects on circuit patterns and defects such as electrical open/short-circuits can be detected automatically by executing various inspections of the type for comparing the images obtained through radiation of white beam, laser beam and electron beam with the adjacent similar patterns in the substrate of semiconductor device including fine circuit patterns. However, such inspection instrument provides the positional information generated by a defect and the size of defect. In order to obtain detail contents of defect, it is required to acquire again a high resolution image at the defect generating area and classify the contents of defect from the image information in regard to the figure, roughness and material and others.

In the related art, even in the length measuring SEM and review SEM, a beam current radiated to a sample has been reduced, a plurality of images of the same area have been obtained and added to form an image in order to review the fine figure in higher resolution. In such an image forming method, a fine figure can be reviewed but it has been difficult to review electrical defects through the voltage contrast. In other words, when the open or short defect detected with the wafer inspection system using electron beam is reviewed with the review SEM, the defect often cannot be recognized.

The inventors of the present invention have found that the review area must be charged to review an electrical defect using the voltage contrast and a large beam current to be radiated is preferable for better charging. However, since it is also required to obtain the voltage contrast and execute the detail surface review in the same review process, a beam current that can maintain high resolution must be selected. Moreover, the same inventors have found that various electrical defects can be reviewed with the same instrument by adequately changing the beam scan speed depending on contents of electrical defects.

The inspection instrument of related art has a problem that a large amount of steps such as beam axis adjustment and luminance adjustment is required to change the optical conditions for radiation of electron beam and detecting conditions thereof because various parameters of instrument are fixed only to review the fine figure. However, as is already explained, electrical defect must also be reviewed together with fine figures with the same instrument and therefore simple setting must be assured for the electron beam radiating condition for reviewing of figures, conditions for reviewing figures and conditions for reviewing electrical defects.

The inventors of the present invention have also found that different electron beam radiating conditions, lens conditions and signal detecting conditions can be set easily by storing and registering the files of the conditions suitable for fine figure review as the "figure review mode", the conditions suitable for review of roughness as the "roughness review mode" and the conditions suitable for review of electrical defect as the "voltage contrast review mode".

Moreover, as the electron beam radiating conditions, small beam current is preferable for high resolution review in the "figure review mode". On the other hand, in the "voltage contrast review mode", a large radiation beam current is preferable for more effective charging of the sample surface since review is conducted using the phenomenon that brightness of SEM image is different in the normal circuit pattern and defect generating pattern because amount of secondary electrons reaching the detector changes depending on electrical characteristic when the surface is charged and energy of secondary electrons generated from the surface of sample also changes. Moreover, the charging condition of the sample surface can be controlled and defective area can also be visualized from the SEM image by changing the electron beam scan speed depending on contents of electrical defect. In the "roughness review mode", it is not particularly required to control the beam radiating conditions because this mode is not easily influenced by the radiated beam current and scan speed.

Next, the same inventors have also found the following conditions to detect the signal that is generated simultaneously generated from the sample surface when the sample surface is radiated with the electron beam. In the "figure review mode", the secondary electrons generated from the surface of sample are detected and in the "roughness review mode", the reflected electrons are detected. In the "voltage contrast review mode", only the secondary electron of the predetermined energy among the secondary electrons is detected in order to obtain respective information pieces. Therefore, it has also been found that the information pieces of "figure", "roughness" and "voltage contrast" can be individually visualized and detected by detecting as explained above the secondary electron and reflected electron generated from the surface of sample when the surface is radiated with the electron beam.

Moreover, it has also been found that the "roughness" can also be reviewed simultaneously by detecting the reflected electron simultaneously with the figure through detection of the secondary electron in the "figure review mode". In the same manner, the "roughness" can also be reviewed simultaneously by detecting the reflected electron at the time of detecting the secondary electron having higher energy in the "voltage contrast review mode".

Next, it has also been found that the adequate review conditions can be set on the occasion of reviewing the defect by setting the "figure review mode" in the wafer inspection and defect inspection after inspection using laser because electrical defect cannot be detected in the wafer inspection and inspection using laser and on the other hand, the adequate review conditions can be set automatically at the time of reviewing the defect by setting the "voltage contrast review mode" in the defect inspection after execution of the wafer inspection to detect electrical defect.

In addition, it is also found that the target defect can be reviewed easily when the electron beam radiating conditions and signal detecting conditions can be set depending on the selection by providing an input image for selecting the "figure review mode" and "voltage contrast review mode" in the interface image and then selecting the review mode from this input image. Moreover, in regard to the "roughness review mode", the "roughness" can be reviewed freely even in the "figure review mode" and "voltage contrast review mode" by selecting the "roughness review mode".

The review for fine figure and roughness information and review for electrical defect can be realized freely depending on the purpose by executing these inspection methods and using the inspection instrument including these functions. A means for realizing the inspection method in the present invention will then be explained hereunder.

According to the present invention, as the first means, the electron beam radiating and signal detecting conditions that is suitable for voltage contrast review can be set. As the condition suitable for voltage contrast, a beam current is set to a comparatively higher level, radiation energy is set to a comparatively higher level and scan speed is set to comparatively higher rate for the open defect but to lower rate for the short defect. Moreover, in regard to the detection system, an energy filter is used to provide a function to detect only the signal having the energy larger than the predetermined energy applied to the energy filter in view of discriminating a difference between amounts of secondary electrons in different energy distributions generated from the normal area and defective area due to the influence of surface potential. Thereby, electrical defect can be recognized with the voltage contrast in comparison with the existing method to review, without use of the energy filter, in the same condition that a beam current is small.

As the second means, any review condition can be set easily almost without any adjustment by registering, as the table or file, various electron beam radiating conditions and signal detecting conditions that are suitable for recognition of electrical defect explained in above first means as the "voltage contrast review mode", then registering various electron beam radiating conditions and signal detecting conditions that are suitable for fine figure review as the "figure review mode" and moreover registering the signal detecting condition that is suitable for review of surface roughness and height as the "roughness review mode".

As the third means, various filtered energy signals are individually detected by providing an energy filter in the signal detecting system and allocating a plurality of detectors under the electron beam radiating condition that is suitable for review of voltage contrast described for the first means explained above. Thereby, the "voltage contrast mode", "figure review mode" and "roughness review mode" can be set by changing only the detecting condition in the same electron beam radiating condition by reviewing the figure information with the detecting signal mainly formed of secondary electron, the surface roughness information with the detecting signal mainly formed of reflected electron and voltage contrast with the detecting signal mainly formed of secondary electron having higher energy level. Namely, adjustment of optical axis is no longer required.

As the fourth means, highly accurate positioning can be realized even in the case of extracting a sight of defect at the area separated from a die to which alignment is performed by obtaining images of the circuit pattern for alignment in the first die and the circuit pattern for alignment in the second die and then also obtaining not only the compensated information of positional deflection and rotation but also the error of magnification factor of the coordinate system at the time of executing the alignment of positional information of two dies.

As the fifth means, more highly accurate compensation for position can be realized by further reviewing the predetermined particles and defects after the alignment of position and rotation using the predetermined pattern and then further compensating for he position information from the position of particle/defect within the sight.

As the sixth means, the above "voltage contrast review mode" and "figure review mode" or the like can be set automatically by reviewing, with the review SEM, the detection result information including coordinate data of defect and the code of inspection instrument when the inspection is executed with an inspection instrument and the result is output to the external circuit. Namely, conditions for automatically executing the review can be set easily by automatically selecting the figure review mode" when the defect data obtained by inspection with a wafer inspection instrument and an inspection instrument using laser beam that cannot detect an electrical defect and also setting the "voltage contrast review mode" depending on the inspection conditions when the defect data obtained by the wafer inspection system using electron beam that can detect electrical defect is read.

As the seventh means, automatic setting of review can be realized easily by allocating, within the image, an input unit for selecting the review condition such as "voltage contrast mode", "figure review mode" and "roughness review mode" and also allocating an input unit for selecting the review area at the image for setting the review condition with review SEM.

As the eighth means, a means is provided for switching the review sequence from the nearer defect in the process to automatically execute the review/image review/ classification of defect contents for a plurality of defective areas with the review SEM.

As the ninth means, review conditions can be set easily through the process that the detail instrument conditions are not displayed in direct in the main menu as the sub-menu by providing, in the display image for setting the review conditions, the main menu display image to select the inspection conditions in order to set the review conditions with the simplified menu selection.

Thereby, the important parameter input for review can be realized only with the interface operations for selecting the menu without the complicated input operations.

With the means explained above, not only the surface figure review of the prior art but also the review of electrical defect can be realized in the inspection of the substrate having a fine circuit pattern as well as the semiconductor device to review the details of detected defect. Moreover, the adequate review conditions can be set easily without any adjustment of optical axis as required by previously registering the review condition suitable for figure review and the condition suitable for electrical defect review as the instrument condition for enabling the selection in the setting condition file to determine the inspection condition. Moreover, the highly accurate sight detection of defect can be realized by executing magnification factor compensation by two points in the alignment and the positional information compensation by actual defect and particle. In addition, review conditions can be set easily by displaying, in the interface display image of inspection instrument, the condition file having an input unit for determining the review mode and review area.

The electrical defect that has been difficult for review with the prior art can be reviewed easily, moreover review condition setting and instrument adjustment that have required a longer time in the review of electrical defect can be realized only with the simplified operation such as selection of review condition file and moreover the review parameter setting that have required a longer time in generation of the review condition file can be realized efficiently within a short period of time by reviewing a substrate having a circuit pattern, for example, a semiconductor device using the review method and review system explained above after the review thereof with an inspection system. As a result, the detail contents of the figure defect of pattern, fine particles, electrical continuity defect and short-circuit generated in the process of the steps for manufacturing a semiconductor device can be detected quickly and problems included in the process or manufacturing system condition can then be visualized. Therefore, the cause of defect in the manufacturing process of each substrate as well as the semiconductor device can be searched in the higher speed with higher accuracy than that in the existing method and instrument. As a result, higher manufacturing yield, namely lower failure rate can also be assured and simultaneously TAT until an adequate measure is taken from detection of defect can also be reduced.

BRIEF DESCRIPTION OF THE DRAWINGS

FIG. 5 is a diagram illustrating the condition of each review mode.

DETAILED DESCRIPTION OF THE PREFERRED EMBODIMENTS

The pattern inspection system and the method of inspecting pattern of the present invention will be explained in detail with reference to the accompanying drawings.

In this embodiment, an inspection method and an inspection system will be explained to form an image using electron beam in order to detect existence of defect on a circuit pattern from such image and classify the contents of defect for the circuit pattern that is already inspected with the other inspection system. Here, as an example, inspection of a circuit pattern of a semiconductor device formed on a wafer will be explained.

Figure 1:
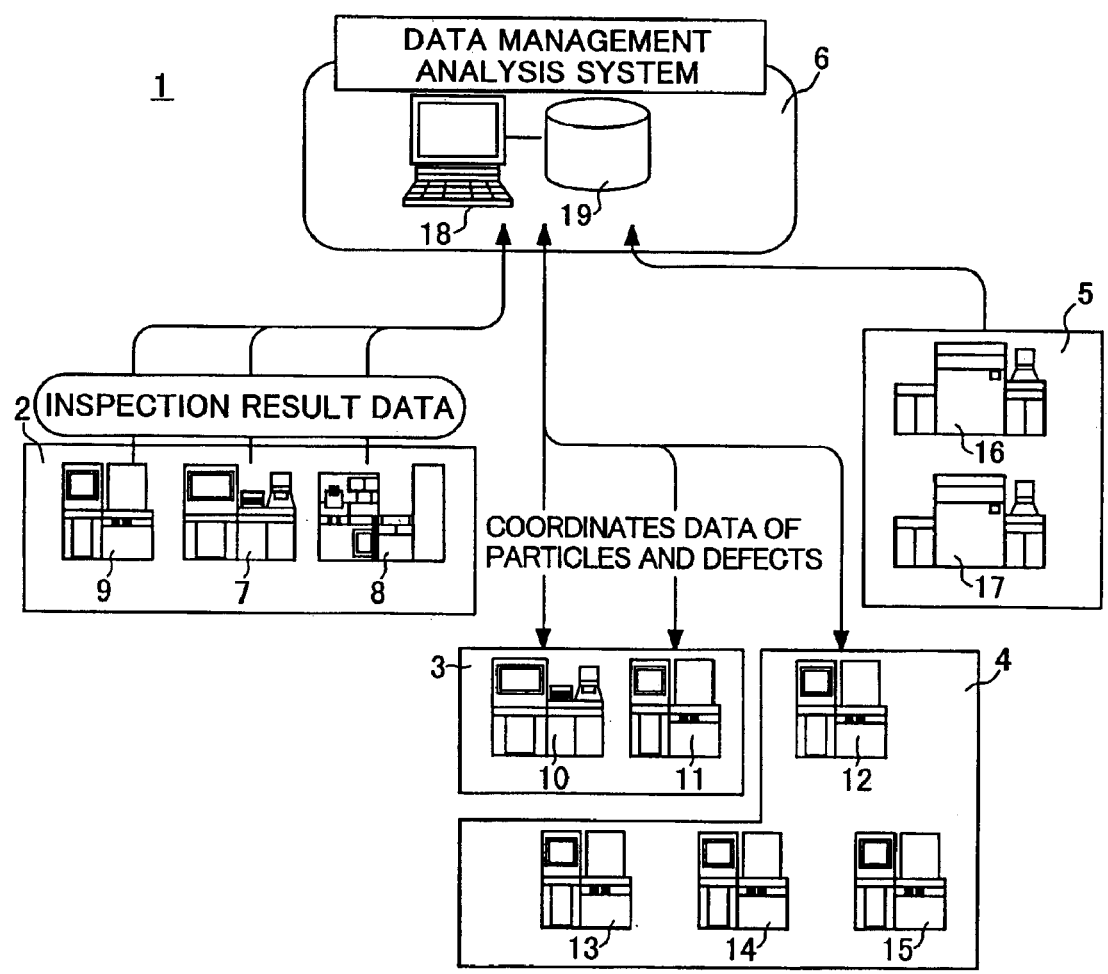
FIG. 1 is a schematic diagram illustrating an example of the pattern inspection system with the present invention.

First, the outline of a pattern inspection system using a pattern inspection system of the present invention is illustrated in FIG. 1. The pattern inline inspection system 1 includes an inspection system 2 for finding out unknown particles and defects, a review system 3 for receiving an information of coordinates or the like of defect found out by the inspection system 2 to output an image of the defect and classification result of the review by reviewing in detail the contents of defect, an analysis system 4 for receiving also the information of coordinates or the like of defect to execute the cross-section forming process and subsequent various analysis processes, a tester 5 for executing operation tests of wafer and a data management system 6 for intermediating images and coordinate data for the management thereof. As the inspection system 2, a particle inspection system using laser 7, a wafer inspection system 8 and a wafer inspection system using electron beam 10 may be listed. In the review system 3, a review system using white luminescence 10 and review SEM 11 may be listed. As the analysis system 4, a focused ion beam system 12, a high resolution SEM 13, an auger electron spectrum analysis system 14 and a TEM 15 may be listed. As a tester 5, a tester for memory device 16 and a tester for logic device 17 may be listed. As the data management system 6, a server for data management system 18 and a storage for data management system 19 may be listed.

For the wafers in the manufacturing process, the wafers are inspected completely or partly using any one system of the inspection systems 2, but such inspection is conducted periodically with the predetermined process or with the desired process depending on the conditions of defect generation. In such inspection, if the inspection has been executed using the particle inspection system using laser 7, particles and flaws are mainly detected. When the inspection is executed with the wafer inspection system 8, a pattern figure defect and a defect under a thin film that allows transmission of white beam can be detected in addition to particles. When the inspection has been executed using the wafer inspection system using electron beam 9, electrical defects such as non-conductive defect of contact hole, disconnection of wiring, short-circuit of wiring and transistor can be detected in addition to particles and pattern figure defect generated at the surface. These detected defects are then output to the server for data management system 18 of the data management system 6 and is then stored in the storage for data management system 19. Each unit of the inspection system 2 mainly has a function to locate the defective area and therefore the data to be output includes the information pieces such as the number of defects, coordinate information of each defect, size of defect and inspection conditions for inspection with each inspection system of the inspection systems 2.

To set up a measure for defect generated in the manufacturing process, detail contents of defect must be detected to identify the cause of defect and therefore it is required to obtain the information such as an image of defect or content of defect. For this purpose, the process to review the defect detected with the review system 3 is necessary. On the occasion of reviewing the defect with the review system 3, the coordinate data of defect, for example, obtained with the inspection system 2 is read via the server for data management system 18. In the review system using white luminescence 10, an image and classification result can be obtained with an optical microscope unit. However, review by high-resolution review SEM 11 is required to detect fine particle and contents of defect on the fine circuit pattern. Details of structure of review SEM 11 and review method will be explained later.

The analysis system 4 can execute analysis for further fine structure by processing the cross-section or flat surface using the focused ion beam (FIB) system 12, reviewing the surface and cross-section with the high resolution SEM 13 and TEM 15 and analyzing element composition of the predetermined area with the auger electron spectrum AES analysis system 14. These analyses are executed after preparing individual wafers and therefore the wafers to be analyzed are broken. Moreover, since analysis is performed after extracting the analysis area, structure and coordinate system of a sample tray are different to a large extent. Accordingly, it is difficult to obtain the sight in direct based on the coordinate information of defect detected with the inspection system 2. Namely, since these analysis systems 4 can realize detail analysis but destroys the wafer to be analyzed and requires a longer analysis time, these systems 4 use the wafers sampled because of generation of defect as the object of analysis. Moreover, the tester 5 executes the electrical test to each die of the completed wafer in order to search various operating conditions and select the condition.

The inline inspection system 1 collects, with the data management and analysis system 6, the result of inspection of wafer in the manufacturing process with the inspection system 2, the result of search for contents of particle and defect with the review system 3 and the result of electrical test with the tester 5 and then identifies the factor for controlling the yield and the process and instrument that require reduction of defect and forecasts the yield by collating and analyzing the condition of defective operation and yield by the tester 5, inspection condition of various processes and contents of generated particle and defect. Therefore, it is very important to quickly obtain and classify, with higher accuracy and efficiency, the image including detail information detected through the inspection with the inspection system 2.

The existing review SEM 11 is intended to realize the high-resolution review for fine figure by squeezing an electron beam current to a narrow beam. Therefore, this review SEM 11 can perform the high resolution review for the particle and defect having the surface roughness that have been detected with the particle inspection system using laser 7 and for the pattern figure defect that has been detected with the wafer inspection system 8. However, such review SEM 11 cannot review the electrical defects of semiconductor transistor such as continuity defect of contact hole, disconnection of wiring, short-circuit of wiring and short-circuit of transistor that can be detected with the wafer inspection system using electron beam 9. Since this review system 3 is used to review in detail the detected defective area and output the classified content of defect, it is very important to recognize whether the defect detected with the other inspection system has been detected erroneously or not and to also recognize the contents of defect. Therefore, when the inspection result of this embodiment is considered here, there will be explained the review SEM and review (inspection) method that can recognize contents of defect and realize classification through the discrimination based on the SEM image for particle (including identification of the kinds of particle) and pattern figure defect (including disconnection/short-circuit, flaw and figure defect), non-conductivity of contact hole and short-circuit of transistor at the lower layer.

The review SEM 20 and review method of the present invention corresponding to the review SEM 11 of the inspection system 1 explained in regard to FIG. 1 will be explained hereunder.

Figure 2:
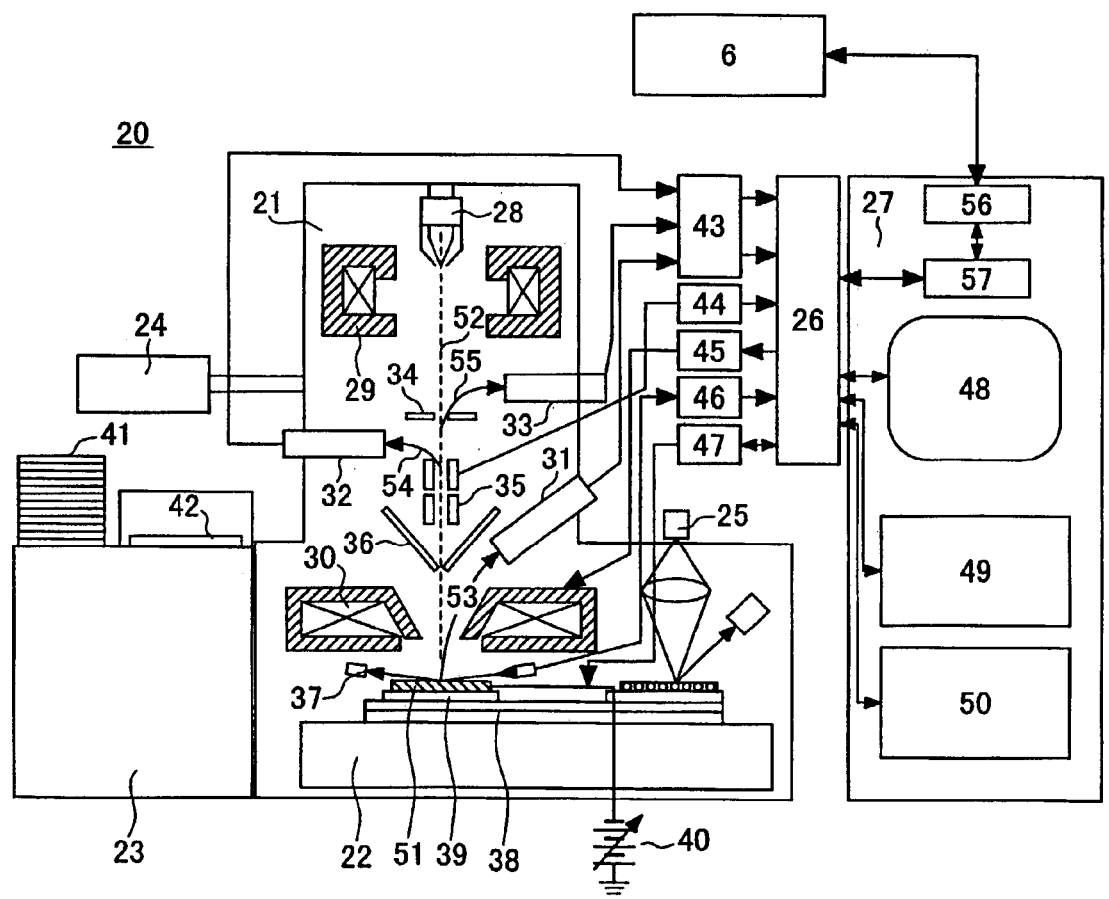
FIG. 2 is a diagram for explaining an embodiment of a pattern inspection instrument of the present invention.

FIG. 2 illustrates an embodiment of the pattern inspection system of the present invention and also an example of structure of the review SEM 20. This system comprises an electron beam optics unit 21, a stage unit 22, a wafer handling unit 23, a vacuum unit 24, an optical microscope unit 25, a control unit 26 and a user interface unit 27. The electron beam optics unit 21 is constituted of an electron gun 28, a condenser lens 29, an objective lens 30, the first detector 31, the second detector 32, the third detector 33, an energy filter 34, a deflector 35, a converter electrode 36 and a wafer height measure sensor 37. The stage unit 22 is constituted of an XY stage 38, a wafer holder 39 for setting a wafer as a sample and a retarding power supply 40 for impressing a negative voltage to the wafer holder 29 and wafer 51. The XY stage 38 is provided with a position detector based on the laser measuring system. The wafer handling unit 23 is constituted of a wafer case hold unit 41 and a wafer loading unit 42 and the wafer holder 39 goes forward and backward between the wafer loading unit 42 and XY stage 38 under the condition of loading the wafer 51. The control unit 26 is constituted of a detector unit control unit 43, a beam deflection control unit 44, an electron optics control unit 45, a wafer height measure sensor unit 46 and a robotics/stage control unit 47. The user interface unit 27 is constituted of a graphical user interface 48, an image processing unit 49 and an image/inspection data storage unit 50.

Figure 3:
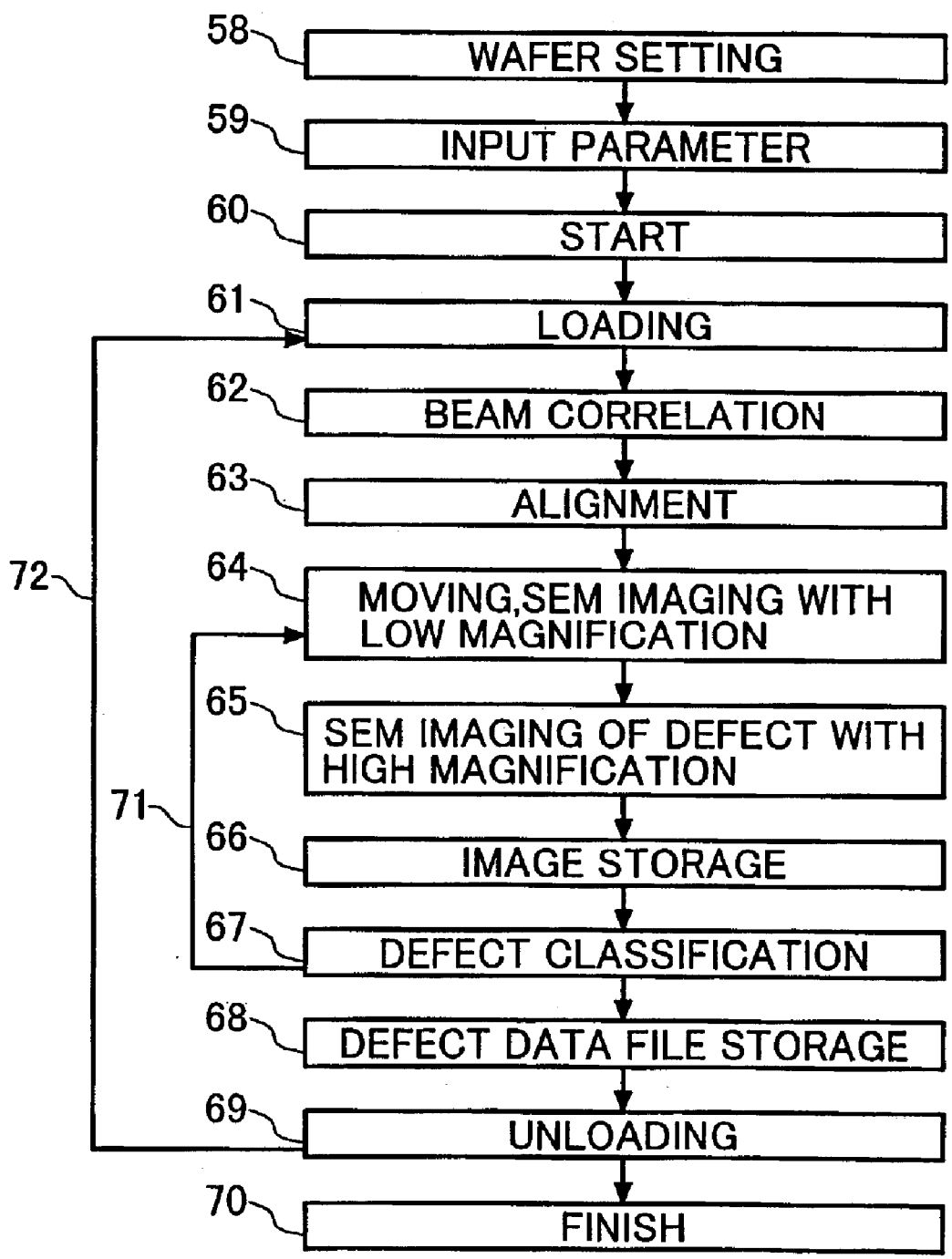
FIG. 3 is a flow chart illustrating an example of the inspection flow of the present invention.

Next, operations of respective portions of FIG. 2 will be explained using the flow-chart of FIG. 3. This flow-chart is provided to automatically execute the review.

First, in the step 58, a wafer cassette wherein the wafers 51 are set in the desired racks is placed on the wafer case hold unit 41 of the wafer handling unit 23 of FIG. 2.

Next, in the step 59, in order to designate the wafer 51 to be reviewed, the rack number in the cassette wherein the wafer 51 is set is designated from the graphical user interface 48. Moreover, in the review, as is already explained above, the inspection result file is selected from the graphical user interface 48 to execute the review using the electron beam image on the basis of the inspection result information including the position information of defect obtained by execution of inspection with the other inspection system. At the time of selection, it is possible to read the inspection result file through the communication using the network or to read the inspection result file from a medium such as FD and MO. In any case, various data of inspection result can be read to a data input unit 56 by designating the inspection result file name and such data can be converted to the data format and coordinate system used in the review SEM 20 with a data transfer unit 57. Moreover, a review condition file name is input from the graphical user interface 48. This review condition file is formed by combining various parameters to determine the contents of review. Contents of review condition file and setting method will be explained later. Moreover, in the case where a plurality of wafers are automatically reviewed continuously, the inspection result file name and review condition file name are input as explained above to each waver to be inspected. The condition setting can be executed freely as many times as 25 sheets×2 cassettes for the continuous automatic review. Upon completion of condition input that is required for execution of these reviews, the automatic review sequence can be started in the step 60.

When the automatic review is started in the step 61, the preset wafer 51 is carried first into the review system. In the wafer handling unit 23, even if the diameter of wafer to be inspected is different or the shape of wafer is different such as the orientation flat type or notch type, the wafer holder 39 for setting the wafer 51 can be exchanged depending on the size and shape of the wafer. The wafer to be inspected can be set on the wafer holder 39 from the cassette with a wafer loading unit 42 including the arm and auxiliary vacuum chamber.

In the step 62, when the wafer 51 is loaded, the electron beam radiating condition is set to each unit with the electron optics control unit 45 based on the input review condition. The electron beam image of the predetermined position of wafer 51 is obtained and the focal point and non-focal point are aligned. Moreover, simultaneously, height of wafer 51 is obtained from the wafer height measure sensor 37, correlation between the height information and focusing condition of electron beam is obtained to automatic adjustment to the focal point condition from the result of wafer height detection without subsequent execution of every focusing operation when the electron beam image is obtained. Thereby, the electron beam image can be obtained at a high speed.

Figure 4:
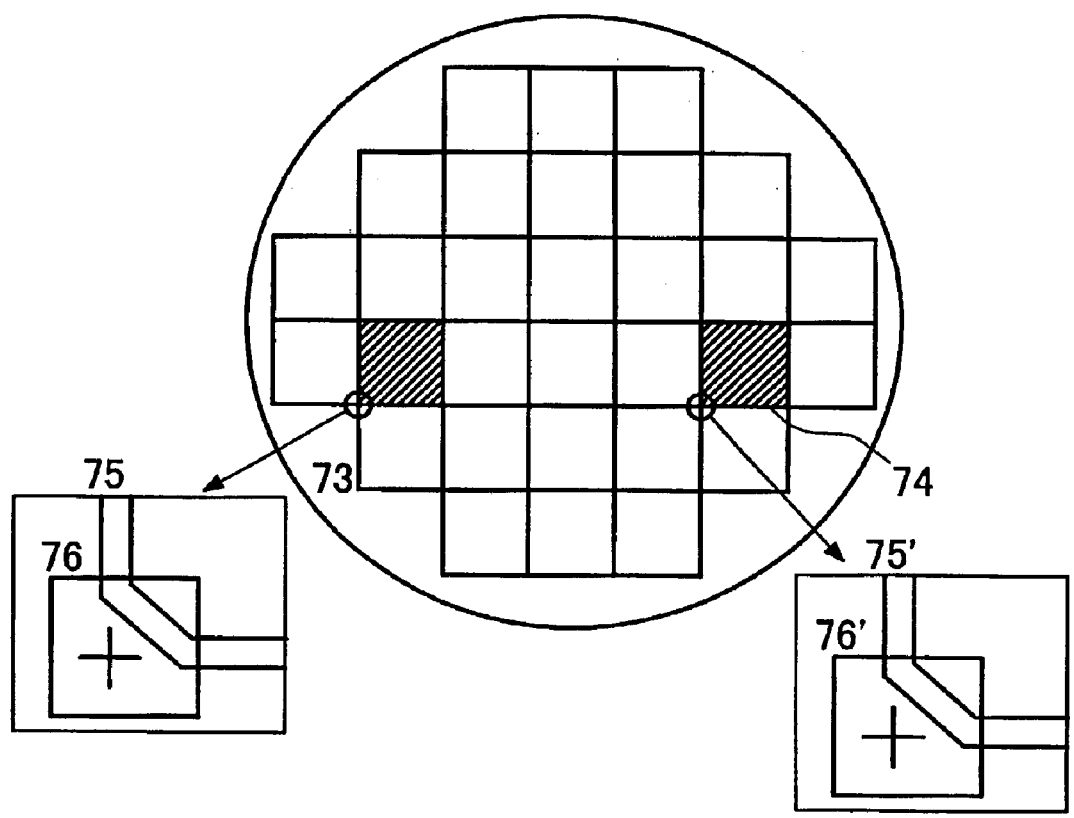
FIG. 4 is a diagram illustrating an example of the alignment method.

Upon completion of adjustment for electron beam radiating condition and focal point/non-focal point, the alignment at the two points of wafer is executed in the step 63. Further using FIG. 4, the alignment method in the review SEM 20 of the present embodiment will be explained. In view of executing the automatic alignment required for automatic review, it is essential to read the optical microscope image and SEM image of the chip for alignment, pattern formed for alignment and the pattern suitable for alignment, preset coordinate and dictionary information in the review condition input in the step 59 using the wafer having the pattern identical to the wafer to be reviewed. In the review, it is also essential to obtain the sight of the position of defect with higher accuracy. Therefore, prior to the acquisition of sight of defective area, automatic alignment is executed using the alignment condition and alignment image registered in the above method.

As already explained above, the optical microscope image 75 and electron beam image 76 of the designated area where the pattern for alignment exists are previously registered in the memory and the image name and designated two points coordinates (X1, Y1), (X2, Y2) of the alignment target are registered in the review condition file. During the alignment process, when the pattern for alignment on the first chip 73 exists, the sample tray moves to the coordinate registered on the inspection condition file, an image is obtained with the optical microscope unit, the area matching with the optical microscope image that is already registered with the image process is searched automatically and when such area is detected, the coordinates of the detected point is calculated with arithmetic operation. The electron beam image 76 of the same point is obtained based on the detected coordinates, the area matching with the electron beam image that is already registered with the image process is searched automatically and when such area is detected, the coordinate (X1, Y1) of the detected point is calculated with the arithmetic operation and this coordinate is then stored as that of the first chip.

Next, in regard to the second chip 74 located at the parallel position on the matrix of the circuit pattern, the stage is moved to the position where the alignment pattern is assumed to exist. Therefore, like the first chip, the area matching with the image that is already registered with the image process in the optical microscope image 75' and electron beam image 76' is searched and the coordinate (X2, Y2) of the detected point is calculated with the arithmetic operation and it is then stored as the coordinate of the second ship. An rotating amount θ of the circuit pattern layout on the substrate to be inspected for the stage moving direction is obtained from the deviation of coordinates between two points of the alignment mark position (X1, Y1) on the first chip, the assumed position of the second chip calculated from the chip size data and the coordinate position of (X2, Y2) obtained through actual acquisition of image, namely from the deviation amount in the X and Y directions and amount of compensation in the direction of scanning the electron beam is determined from this rotation amount θ.

Moreover, it is also possible to detect the positions of alignment patterns (X1, Y1; X2, Y2), calculate the offset value and magnification factor of the coordinate system from such coordinate values and detect the inspection area and inspection start point in alignment with the position of the circuit pattern on the wafer to be inspected. In the prior art, only the rotation amount θ of the pattern layout has been calculated in this alignment and the compensation for magnifying factor of the coordinate system has not been executed. As a result, in the acquisition of sight of defect after execution of alignment, a defect is deviated from the center as the chip becomes far from the alignment execution chip. In this embodiment, the positional offset and magnification factor error in the X direction are obtained from not only the rotation amount θ but also from deviation amount of pattern coordinate and the magnification factor error in the Y direction can also be calculated from such magnification factor error. Thereby, the problem that the defect is perfectly deviated from the sight can be solved and the defect can be reviewed with higher accuracy.

Upon completion of alignment, rotation and coordinate value are compensated on the basis of the result of alignment and the XY stage 38 moves to the position of the defect to be reviewed based on various information pieces of the already read inspection result file in the step 64. A method of selecting the defect to be reviewed will be explained later. Upon completion of movement of the XY stage 38, highly accurate position is obtained with a laser measuring system mounted on the XY stage 38 and the beam is radiated to the wafer 51 by compensating for the electron beam radiating position with the beam deflection control unit 44 to bring the defect about the center of sight based on this stage position information. Since a defect is located within the sight considering the coordinate error of the other inspection system, the first image can be acquired with a comparatively low magnification factor. For example, the image of low magnification factor can be obtained with a size of sight of about 10 to 15 μm2. In this embodiment, the review magnification factor is set to the fixed magnification factor previously registered to the review condition file in the automatic review sequence.

When the image of the position corresponding to the coordinate of defective area is obtained in the step 65, it is transferred to the image processing unit 49 via the signal detector unit 43. Thereafter, the XY stage 38 moves to the adjacent chip to obtain the image of the same pattern in the adjacent chip under the same condition and then also transfers the image to the image processing unit 49. The image processing unit 49 executes alignment of two sheets of images and image comparison to recognize e detail position of defect and size of defect. The XY stage 38 moves again to e coordinate of defective area and adjusts the electron beam radiating position with the beam deflection unit 43 to bring about the defective area to the center with the defect position information within the image in order to obtain the image of defect ye area with a comparatively higher magnification factor. For example, when the image is obtained again, the image shall have the size of sight of about 1 to 3 μm2.

In this embodiment, the magnification factor of review is set to the fixed magnification factor that is previously registered to the review condition even when the high magnification factor can be obtained. In the case of the method of the other embodiment, for example, the size of defect can be detected with a higher accuracy on the occasion of recognizing the defective area when the image is obtained with the low magnification factor in the step 64. Therefore, it is also possible to automatically change the magnification factor to obtain the size of defect where the defect occupies the area, for example, of 69% of the image.

In the step 66, the high magnification factor image obtained is stored as required in the image/data storage unit 50. Storing/non-storing is previously set in the review condition file. Moreover, it is also possible to simultaneously store, as required, the images of a plurality of kinds from a plurality of detectors depending on the setting. For example, the image of the secondary electron detected with the second detector 32 and the image of the reflected electron detected with the first detector 31 can be stored simultaneously.

In the step 67, an image is stored and simultaneously the image processing unit 49 extracts the characteristics of defect from the image information and automatically classifies the contents of defect. The classified result is coded, for example, with the numerals of 0 to 255 and this coded number is written to the area corresponding tot the defect classifying code in the inspection result file. Thereby, the code indicating the classification result is automatically written for the reviewed defect in the inspection result file.

A series of operations of movement to the defective area→acquisition of low magnification factor image→recognition of defective area→acquisition of high magnification factor image→storage of high magnification factor image→classification of defects→input of classification result to the inspected defect file is repeated as many times as the number of reviews as indicated in step 71. In the step 68, when a series of operations is completed for all defects to which execution of review is designated on a sheet of wafer, the inspection result file of wafer (file to which the classification result is input) is automatically stored, the inspection result file is output to the designated destination and the wafer is then unloaded in the step 69.

Thereafter, a series of operations from output of inspection result file and unloading from the loading of wafer is repeated as illustrated in the step 72 as many times of the number of designated wafers and when the review is completed for all wafers to which execution of review is designated, the automatic sequence is completed in the step 70.

A method of setting the review conditions in this automatic review sequence will then be explained below. The review condition file includes the review mode formed of the electron beam radiating condition to determine the image quality as the object and signal detecting condition, review sampling including the number of review points and ADR (Auto Defect Review)/ADC (Auto Defect Classification) condition to automatically execute the review. The ADR/ADC condition includes the magnification factor (low magnification factor, high magnification factor) of image for alignment and during the review, electron beam radiating condition in each mode (such as electron beam current, condenser lens condition, objective lens condition, detector, energy filter condition or the like) and automatic classification condition (image processing condition), and image storage condition, etc.

Contents of review mode to determine the image quality to be obtained, namely the electron beam radiating condition and detecting condition among various review conditions will be explained with reference to FIG. 2 and FIG. 5.

As explained above, the inventors of the present invention have found that the area to be reviewed must be charged and a larger radiation beam current is preferable for more effective charging for reviewing electrical defect by using the voltage contrast. However, since it is necessary to obtain the voltage contrast and execute the detail surface review in the same review process, it is required to select a beam current that can maintain the high resolution. For this purpose, the inventors have also found that various electrical defects can be reviewed with the same instrument by adequately changing the beam manipulation speed depending on the contents of electrical defects.

The existing instrument also has a problem that a large amount of processing steps such as adjustment of beam axis and adjustment of luminance or the like are required to change the optical condition and detecting condition of electron beam radiation because various parameters of the instrument are fixed only for the purpose of reviewing the fine figures. However, as is already explained above, it is required to review the fine figures and electrical defects with the same instrument to classify and detect the contents of defect detected with various inspection instruments and the electron beam radiating condition to review the figure, condition to review roughness and condition to review electrical defect must be set easily.

The same inventors have also found that different electron beam radiating condition, lens condition and signal detecting condition can be set easily by filing the condition suitable for review of fine figure as the "figure review mode", the condition suitable for review of roughness condition as the "roughness review mode" and the condition suitable for review of electrical defect as the "voltage contrast review mode" and then storing and registering such files. Moreover, as the electron beam radiating condition, a lower beam current is preferable for high resolution review in the "figure review mode". Since the "voltage contrast review mode" is selected to execute the review by utilizing the phenomenon that brightness of the SEM images differs in the normal circuit pattern and the defect generating circuit pattern because the amount of secondary electron reaching at the detector changes depending on the electrical characteristic and the energy of secondary electron generated from the surface of sample when the surface is charged. Moreover, the surface charging condition can be controlled and the defective area can also be visualized from the SEM image by changing the electron beam scan speed depending on the contents of defect. On the other hand, the "roughness review mode" is not easily influenced by the radiation of beam current and scan speed and therefore it is not particularly required to control the beam radiating condition.

Next, the inventors have also found, in regard to the condition to detect the signal that is generated as the secondary signal from the surface of sample when the sample surface is radiated with the electron beam, that the secondary electron generated from the sample surface is detected in the "figure review mode" and the reflected electron is reviewed in the "roughness review mode" and each information can be obtained by detecting only the secondary electron having the energy that is higher than the predetermined energy among the secondary electron in the "voltage contrast review mode". Therefore, the information piece of "figure", "roughness" and "voltage contrast" can individually visualized and detected by individually detecting the secondary electron and reflected electron generated from the sample surface as explained above when the electron beam is radiated to the sample surface.

The same inventors have also found that the figure can also be reviewed by detecting the secondary electron in the "figure view mode" and simultaneously "roughness" can also be reviewed by separately detecting the reflected electron and similarly, "roughness" can also be detected simultaneously by separately detecting the reflected electron when the secondary electron having higher energy is detected in the "voltage contrast review mode".

FIG. 5 illustrates the conditions that are suitable for respective reviews in such a case that the quality of electron beam image is roughly classified, from these results, to the three kinds of figure review mode (secondary electron image), voltage contrast review mode (voltage contrast image) and roughness review mode (reflected electron image). First, the secondary electron image is suitable for review of material and figure and is also suitable for review of an ordinary particle and figure defect. In the case of reviewing this secondary electron image, it is preferable to set the primary beam current for radiation is set to the range from several pA to several tens of pA. On the other hand, in the case of reviewing the voltage contrast image, more clear contrast can be obtained due to the difference of secondary electron amount and energy reaching the detector when there is potential difference at the surface due to the charging and therefore the beam current of the primary beam for radiation must be set to the range from several tens pA to 200 pA. In the case of the reflected electron beam image that is suitable for roughness review, it is not required to designate the beam current.

Moreover, in regard to the electron beam scan speed, an image of high S/N can be obtained even with a less beam current by displaying the image of TV scanning through additions of images of several tens of images, for example, the 64 images in the ordinary figure review. Accordingly, in the secondary electron image for figure review, several tens of images are added and obtained in the TV scanning. On the other hand, the same inventors have also found that the adequate scan speed is different depending on the kind of defect to be reviewed in the voltage contrast image. For example, in the case of the open defect where the transistor or contact hole is not conductive, it can be reviewed with the image obtained by adding several tens of images in the TV scanning as in the case of figure review.

However, in the defect where transistors have generated the short-circuit or the transistor and wiring have generated the short-circuit, difference between the normal area and defective area can be obtained easily when the scan speed is lowered and the electron beam is radiated. For example, when eight images are added in the low-speed scanning that is lower than the TV scanning by eight times, the image having the S/N that is almost equal to that of the image obtained by adding 64 images in the TV scanning can be obtained and thereby clear contrast of the short defect can be obtained. Therefore, in the voltage contrast mode, when content of defect can be assumed, the scan speed is set to any speed among that explained above for the review. Moreover, such scan speed is set depending on the kind of defect to be reviewed. Otherwise, when a defect cannot be recognized with the review in the TV scanning, the image is acquired again by changing the scan speed. In addition, in the figure review mode, the electron beam radiating energy during the review period is set to 800V to 1 kV. On the other hand, in the voltage contrast review mode, since the voltage contrast can be attained more easily when the lower acceleration beam is used, the radiation energy is set to 500V to 800V. Setting of radiation energy is controllable by changing the retarding power supply voltage impressed to the sample tray.

Next, since the secondary electron, the secondary electron having higher energy for voltage contrast review and reflected electron are individually detected corresponding to each kind of review mode, each electron is detected with individual signal detection system from the characteristic of each signal. First, the ordinary secondary electron image has the energy of secondary electron of about several volts, but when the voltage contrast is formed, it has the energy to which the potential as much as the surface charge is added. Moreover, the reflected election has the energy that is equivalent to the radiation energy. As is explained in FIG. 2, this review SEM 20 has three detectors. The first detector 31 is provided to detect the reflected electron having higher energy. The energy filter 34 is provided between the second detector 32 and the third detector 33 and when the potential that is equal to the retarding potential+several volts to several tens of volts is applied to the energy filter 34, the electron having the energy that is higher than the impressed potential is detected with the third detector 33 and the electron having the energy that is less than such applied potential is detected with the second detector 32. Therefore, the ordinary secondary electron image and voltage contrast image can be detected simultaneously with individual detectors and thereby these images can be formed simultaneously. In addition, the reflected electron including the surface roughness information can also be detected with the individual detector as the signal and thereby the image thereof can also be formed.

In the review SEM in the present invention, the electron beam radiating condition and detecting system condition (selection of detector or the like) can be executed automatically by selecting the review mode with the review condition. Namely, the electron beam radiating condition and signal detecting condition that are suitable for figure review, the electron beam radiating condition and signal detecting condition that are suitable for voltage contrast review and moreover the signal detecting condition for detection of reflected electron in above two modes are previously adjusted and obtained and are also registered. Thereby, when the kind of desired image is selected in the review condition, the selected condition is automatically set.

Detail contents of the review mode and image quality obtained depending on the review mode have been explained above. Next, a method of setting the other review conditions and the user interface image will then be explained using FIG. 6.

Figure 6:
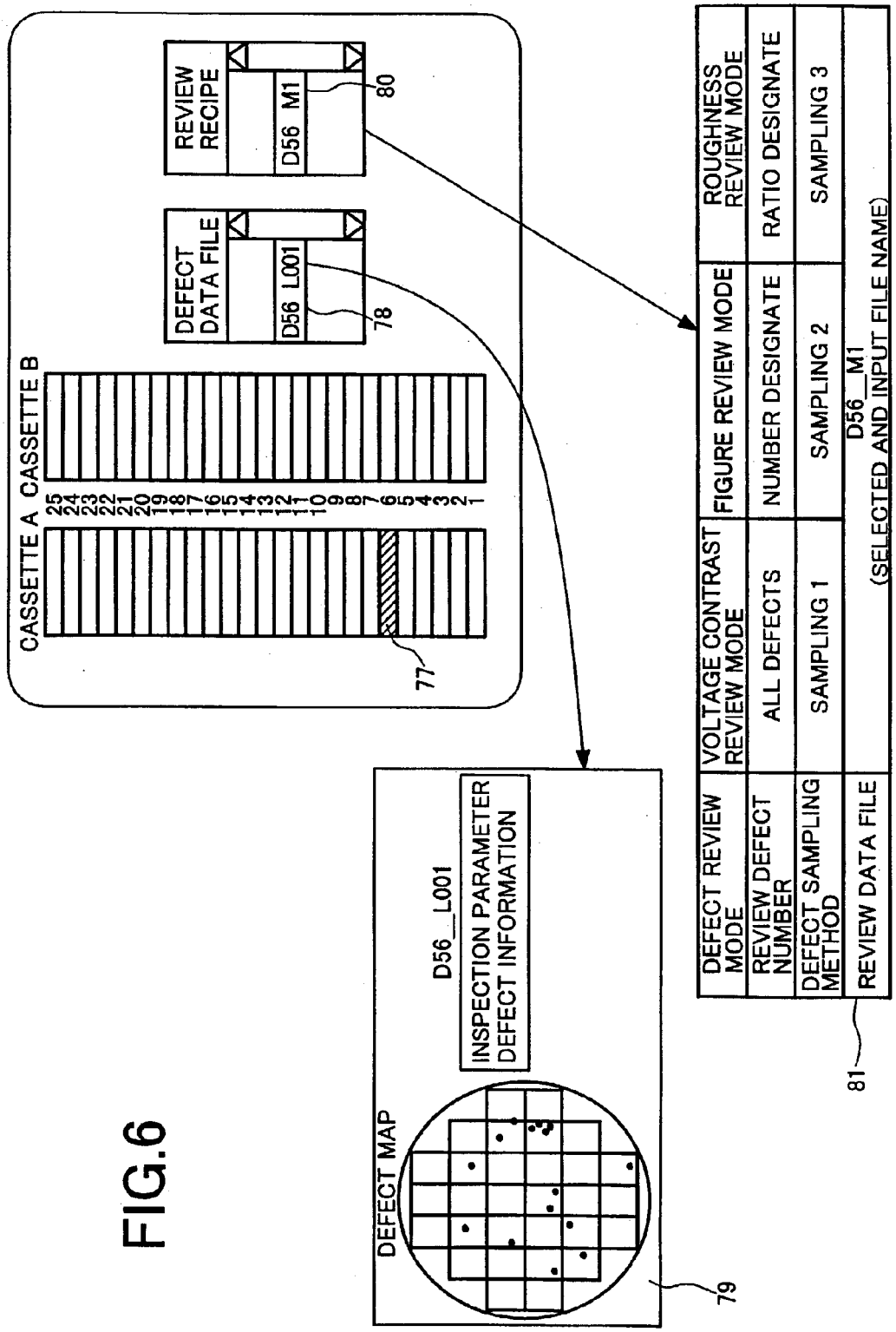
FIG. 6 is a diagram illustrating the inspection condition setting contents and operation method.

FIG. 6 illustrates the graphical user interface for setting the review condition. At the time of executing the review, the cassette in which the wafers to be reviewed are set and the rack number in the cassette are selected as illustrated with the reference number 77. On the occasion of selection, it is enough to click the cassette position in which the wafer to be reviewed is set with a mouse or the like. Next, the defect file that is inspected already for the wafer is selected from the selection dialog 78. In this case, in order to set the content of selected defective file, for example, the number of defects and defect distribution after these are confirmed, distribution and summary are displayed on the image 79 in the review SEM 20 with single-click of mouse, while these are set with double-click. This checking and setting method, the similar effect can be attained, for example, with the right-click for display of summary and left-click for setting.

Next, a review recipe to determine the content of review is selected. The selecting method can be selected from the file previously registered in the dialog 80 as in the case of defect file. Also, in this case, summary of review recipe is displayed in the display image with single-click of mouse and setting can be made with double-click for the setting after checking content of review recipe. In the review recipe, the defect review mode 81 explained above is set. Moreover, the sampling method for selecting the number of defects to execute the review and the defect to be reviewed is also set. In addition, the alignment image for executing the automatic alignment, magnification factor of review (low and high magnification factors of review for the review with the fixed magnification factor, or input of low magnification factor and the ratio of defect within the image for variable magnification factor depending on the size of defect in place of fixed magnification factor), automatic defect classifying condition (for example, content of defect and parameter such as matching rate that are already learned), image storage condition (number of images to be stored and kind of image) and condition for electron beam radiation and detecting system are also included in this review detail condition as the review detail condition and these conditions can also be checked and varied.

As explained above, the wafer to which the review is executed based on the image, the data of defect coordinate for the review and condition for executing review can be set easily and moreover since content of recipe can also be selected, such condition can also be set easily without any complicated input and setting and these data can be managed as the file.

Moreover, on the occasion of setting the review recipe, the defect review mode must be designated but it is previously known that the voltage contrast defect cannot be detected, for example, in the wafer inspection system and wafer inspection system using scattering laser. Therefore, in the review using the inspection result of the wafer inspection system or inspection system using laser, it is also possible to previously set automatically the figure defect review mode. Similarly, in the wafer inspection system using electron beam, since there is higher probability for inclusion of defect detected by the voltage contrast, the voltage contrast review mode is set for the review using the inspection result of the wafer inspection using electron beam. Since the defect file usually includes the code of inspection system, the review mode can be thereby determined automatically when the defect file of the inspection result is selected.

Figure 7A:
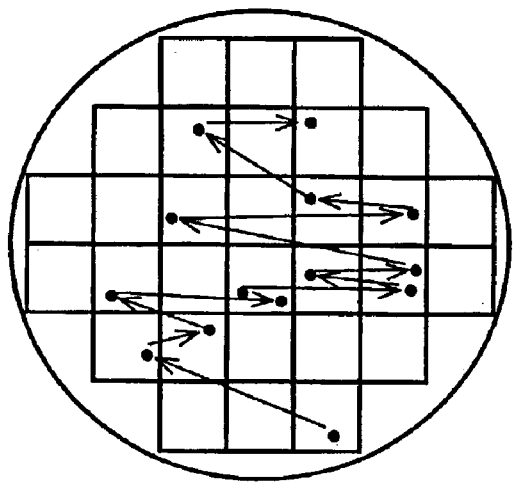
FIGS. 7A and 7B are diagrams illustrating examples of the review sequence.
Figure 7B:
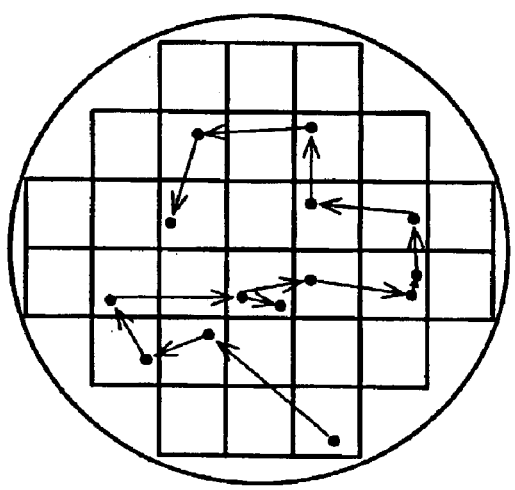

Moreover, in the review SEM 20, the nearer defect is selected first in the case of reviewing a plurality of defects in order to improve the speed of review. FIGS. 7A and 7B illustrate examples of review sequence. In the related art, for example, as illustrated in FIG. 7A, the defects have been reviewed in the sequence of detection of defect or chip. However, in order to realize automatic review of the defects exceeding 500 points within the period of an hour, the moving distance of stage and moving time must be minimized and therefore as illustrated in FIG. 7B, the stage is moved to the nearest defect. Thereby, the review in the higher speed than the existing method can be realized.

In addition, existence in generation of defect is not yet detected until the electrical test is executed with the tester 5 to the wafer or chip that has completed the manufacturing process and analysis has been executed requiring a longer time with the analysis system 4 even in the analysis to identify the cause of defect, but electrical defect can be detected quickly in the manufacturing process and content of defect can be detected quickly with higher accuracy with the review SEM 20 by applying the wafer inspection system using electron beam 9 and review SEM 20 to the inspection system 1. Therefore, several months have been required until the defect is detected and adequate measure is taken for such defect, but such adequate measure can be taken within one day to several days from generation of the defect and thereby efficiency of development and manufacture of semiconductor device can remarkably be improved.

Moreover, as a result of classification of defects with the review SEM 20, the inspection condition of the inspection realized with the wafer inspection system using electron beam 9 can be checked. Namely, since existence of erroneous detection in the inspection result and size of detected defect can be recognized with higher accuracy, content of defect detected with the wafer inspection system using electron beam 9 and sensitivity of detection can be monitored and when a discrepancy is generated in the detection sensitivity, the sensitivity can be fed back to the inspection system 9.

With the inspection system and inspection method explained above, the review and interface to determine the review condition can be performed efficiently in the system in which an electron beam image of a defective area is obtained based on the positional information of the defect detected with the other inspection system and content of defect is classified the image is stored. Moreover, it is also possible, by setting the mode, to easily set the voltage contrast image that has been considered difficult in the review thereof. As a result, electrical defect, figure defect and roughness information can be now classified and moreover content of defect generated on the wafer can be detected accurately. In addition, with discrimination explained above, the automatic flow of the process up to the output can be realized and thereby the high-speed review can also be realized. In comparison with the existing review, the review rate can be improved by several hundreds times.

Moreover, since selection of wafer to be reviewed, selection of defect file including the defect position information inspected with the other inspection system and selection of review condition and the setting method are all simplified, not only the automatic review but also the review condition setting can also be simplified and performed in the higher rate. Accordingly, on the occasion of setting the review condition in many processes of many semiconductor products, condition can be set and executed immediately within a short period time without any delay of review. Therefore, the time required by an operator can be saved, waiting time of product can be saved remarkably and TAT for detecting generation of defect can also be reduced.

With inline execution of the inspection method and instrument for reviewing the wafers inspected with various inspection systems in the semiconductor device manufacturing process as explained above, it is now possible to accurately and quickly detect in detail not only the number of defects but also the content and figure thereof when changes of various manufacturing conditions and generation of irregularity are detected with the inspection system and thereby generation of many defects can be prevented. Moreover, it is now possible to determine efficiently and accurately within a short period of time the inspection condition of wafer to be inspected by applying the wafer inspection system and method of the present invention and as a result generation of defect can be detected in the higher sensitivity through application of highly accurate inspection. In addition, since the time required for detection of content of defect with execution of review can be shortened remarkably, waiting time of product and occupation time of operator can be shortened and defect can be detected more quickly than in the existing instrument and method and thereby productivity of semiconductor device can also be enhanced.

In regard to the structure of the typical inspection instrument and inspection method of the present invention, the flowchart of practical inspection, operation of each unit, flowchart for determining the inspection condition, graphic user interface for inspection and setting of inspection condition and an embodiment of the interface method have been explained above, but the inspection method and instrument formed through combination of a plurality of characteristics explained above can also be applied within the range not departing from the scope of the present invention.

In the inspection method and review system of the related art, only the image obtained from the upper side of the object to be reviewed having roughness at the surface can be acquired, a large amount of adjustment and time is required to review the defect that can be reviewed with the voltage contrast mode and it has substantially been impossible to simultaneously execute the figure review and voltage contrast review. On the other hand, in the case where various defects generated on the substrate of semiconductor device having the circuit pattern are reviewed using the pattern inspection system of the present invention, electrical defects can be reviewed with the adequate conditions with the voltage contrast review mode. Thereby, each content of the figure defect and electrical defect can be discriminated and classified for detection. As a result, content of defect generated on the wafer to be inspected can be detected and the information required to identify the process and instrument as the measures to be taken can also be obtained.

Moreover, a plurality of wafers can be automatically reviewed sequentially and thereby review can be realized efficiently by applying the automatic sequence and review condition setting function in the review process explained above.

In addition, a user can set the adequate review condition without execution of complicated selection and interface operation by providing the function to automatically select the review mode such as figure review mode after the wafer inspection system and the voltage contrast mode after the wafer inspection using electron beam. Moreover, the information of wall wafers can be obtained effectively even in the case of executing the review and classification of the same review points by selecting the review points with the review sampling function before the review.

With the effects explained above, content of defect generated on the wafer can be detected immediately and effectively with higher accuracy. Therefore, the problem that there are defects that requires longer review time or cannot be reviewed because the efficiency has been bad in the related art can be solved through application of the present invention to the substrate manufacturing process and the problem can be immediately detected accurately. Thereby, adequate measure for irregularity can be taken quickly to the substrate manufacturing process and as a result the failure rate of the semiconductor device and the other substrate can be reduced to improve productivity. Moreover, with application of the inspection explained above, generation of irregular event can be quickly detected and adequate measure can also be taken more quickly than the related art and thereby generation a large amount of defects can be prevented. Thereby, as a result, since generation of defect itself can be reduced, reliability of semiconductor device or the like can be enhanced, development efficiency of new products can be improved and manufacturing cost can also be saved.

What is claimed is:

1. A pattern inspection system, based on a defect image that exists in a circuit pattern and positional information of the defect, in which an image of a region including the defect with higher resolution than the defect image is retrieved, comprising:

a plurality of files which store a defect image and positional information of the defect;

means for selecting a file from the plurality of files;

a sample stage holding a sample to be inspected which holds a defect image corresponding to the selected file;

electron beam optics which radiate an electron beam to the sample to be inspected;

a detector unit including a plurality of detectors which detect a secondarily generated signal attributable to the electron beam;

a review condition file which stores an electron beam radiating condition and signal detecting condition, corresponding to review modes of retrieving an image;

means for selecting a review mode from the review condition file;

an electron optic control unit which controls the electron beam radiating condition of the electron beam optics;

a detector unit control unit which controls a signal detecting condition of the detector unit;

wherein one of the electron optic control unit and the detector unit control unit changes one of the electron beam radiating condition and the signal detecting condition; and wherein an image of the region including a position of the defect image selected by the file selecting means with higher resolution is retrieved; and an image processing unit which classifies the retrieved image depending upon a type of defect including electrical defect and a figure defect.

2. A pattern inspection system according to claim 1, wherein the image processing unit includes an inspection result file which stores an encoded result of the classification.

3. A pattern inspection system, based on a defect image that exists in a circuit pattern and positional information of the defect, in which an image of a region including the defect with higher resolution than the defect image is retrieved, comprising:

a plurality of files which store a defect image and positional information of the defect;

means for selecting a file from the plurality of files;

a sample stage holding a sample to be inspected which holds a defect image corresponding to the selected file;

electron beam optics which radiate an electron beam to the sample to be inspected;

a detector unit including a plurality of detectors which detect a secondarily generated signal attributable to the electron beam;

a review condition file which stores an electron beam radiating condition and signal detecting condition, corresponding to review modes of retrieving an image;

means for selecting review mode from the review condition file;

an electron optic control unit which controls the electron beam radiating condition of the electron beam optics; and a detector unit control unit which controls a signal detecting condition of the detector unit;

wherein one of the electron optic control unit and the detector unit control unit changes one of the electron beam radiating condition and the signal detecting condition;

wherein an image of the region including a position of the defect image selected by the file selecting means with higher resolution is retrieved; and wherein the review modes includes:

a figure review mode in which a surface of the sample to be inspected is reviewed;

a roughness review mode in which a texture of the surface of the sample to be inspected is reviewed; and a voltage contrast mode in which a voltage contrast of the sample is reviewed.

4. A pattern inspection system according to claim 3, further comprising a secondary electron detector for enabling detection in the figure review mode.

5. A pattern inspection system according to claim 3, further comprising a reflected electron detector for enabling detection in the roughness review mode.

6. A pattern inspection system according to claim 1, further comprising an energy filter for enabling detection in the voltage contrast mode.

7. A pattern inspection system according to claim 1, wherein the image processing unit classifies the retrieved image depending on a type of image obtained in the review modes which include;

a figure review mode in which a surface of the sample to be inspected is reviewed, a roughness review mode in which a texture of the surface of the sample to be inspected is reviewed, and a voltage contrast mode in which a voltage contrast of the sample is reviewed.

* * * * *